(12) United States Patent
Ostrovsky (10) Patent No.: US 8,636,270 B2
(45) Date of Patent: Jan. 28, 2014

(54) STRUCTURE FOR USE AS PART OF A MEDICAL DEVICE

(75) Inventor: Isaac Ostrovsky, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1195 days.

(21) Appl. No.: 12/336,845

(22) Filed: Dec. 17, 2008

(65) Prior Publication Data

US 2009/0160112 A1 Jun. 25, 2009

Related U.S. Application Data

(60) Provisional application No. 61/015,105, filed on Dec. 19, 2007.

(51) Int. Cl.
*F16F 1/06* (2006.01)

(52) U.S. Cl.
USPC .................. 267/169; 267/182; 604/525

(58) Field of Classification Search
USPC .......... 267/169, 178, 179, 182; 604/523, 525, 604/526, 528, 96.01, 95.03, 95.04
See application file for complete search history.

(56) References Cited

U.S. PATENT DOCUMENTS

| | | | |
|---|---|---|---|
| 3,924,632 A | 12/1975 | Cook | |
| 4,425,919 A | 1/1984 | Alston, Jr. et al. | |
| 4,430,083 A | 2/1984 | Ganz et al. | |
| 4,806,182 A | 2/1989 | Rydell et al. | |
| 5,037,404 A | 8/1991 | Gold et al. | |
| 5,313,967 A | 5/1994 | Lieber et al. | |
| 5,480,382 A | 1/1996 | Hammerslag et al. | |
| 5,562,619 A | 10/1996 | Mirarchi et al. | |
| 5,706,826 A | 1/1998 | Schwager | |
| 5,795,341 A | 8/1998 | Samson | |
| 5,865,800 A | 2/1999 | Mirarchi et al. | |
| 5,951,539 A * | 9/1999 | Nita et al. .................... | 604/526 |
| 6,068,623 A | 5/2000 | Zadno-Azizi et al. | |
| 6,224,587 B1 | 5/2001 | Gibson | |
| 6,240,231 B1 | 5/2001 | Ferrera et al. | |
| 6,352,531 B1 | 3/2002 | O'Connor et al. | |
| 6,352,539 B1 | 3/2002 | Avellanet | |
| 6,589,227 B2 | 7/2003 | Sønderskov Klint | |
| 6,783,510 B1 | 8/2004 | Gibson et al. | |
| 6,907,298 B2 | 6/2005 | Smits et al. | |
| 6,916,285 B2 | 7/2005 | Takase | |
| 6,942,659 B2 | 9/2005 | Lehmann et al. | |
| 6,991,616 B2 | 1/2006 | Bencini et al. | |

(Continued)

FOREIGN PATENT DOCUMENTS

WO WO 96/33763 10/1996
WO WO 00/25849 5/2000

OTHER PUBLICATIONS

Hypotube Shafts, Designing Hypotube Shafts, retrieved from www.creganna.com, Feb. 7, 2007, (2 pages).
Hypotube Shafts, Intermediate Shaft Design, retrieved from www.creganna.com, Feb. 7, 2007, (2 pages).

(Continued)

*Primary Examiner* — Pamela Rodriguez
(74) *Attorney, Agent, or Firm* — Bookoff McAndrews, PLLC (57) ABSTRACT

A low cost, flexible, torqueable structure for use as at least a portion of a medical device comprises a coil formed of a wound element. The coil includes a plurality of adjacent windings. Connected portions of a region between the adjacent windings are formed (by, for example, laser welding) such that torque can be transmitted between adjacent windings.

18 Claims, 8 Drawing Sheets

(56) References Cited

U.S. PATENT DOCUMENTS

| | | |
|---|---|---|
| 7,011,655 B2 | 3/2006 | Thompson et al. |
| 7,037,290 B2 | 5/2006 | Gardeski et al. |
| 7,048,717 B1 | 5/2006 | Frassica |
| 7,070,608 B2 | 7/2006 | Kurz et al. |
| 7,089,063 B2 | 8/2006 | Lesh et al. |
| 7,090,683 B2 | 8/2006 | Brock et al. |
| 7,105,000 B2 | 9/2006 | McBrayer |
| 7,182,764 B2 | 2/2007 | Jenkins et al. |
| 7,905,877 B1 * | 3/2011 | Jimenez et al. ............... 604/525 |
| 2003/0009095 A1 | 1/2003 | Skarda |
| 2003/0130712 A1 | 7/2003 | Smits et al. |
| 2005/0054951 A1 | 3/2005 | Parins |
| 2006/0074442 A1 | 4/2006 | Noriega et al. |
| 2006/0100687 A1 | 5/2006 | Fahey et al. |
| 2006/0111649 A1 | 5/2006 | Zhou |
| 2006/0178653 A1 * | 8/2006 | Shimogami et al. .......... 604/526 |
| 2006/0189896 A1 | 8/2006 | Davis et al. |
| 2006/0241564 A1 | 10/2006 | Corcoran et al. |

OTHER PUBLICATIONS

Hypotoube Shafts, Proximal Design, retrieved from www.creganna.com, Feb. 7, 2007, (2 pages).

Hypotube Shafts, Distal Design, retrieved from www.creganna.com, Feb. 7, 2007, (2 pages).

Assemblies/Cut to Length/Strands/Products/Fort Wayne Metals/The leader in fine medical wire; Assemblies/Cut to Length, retrieved from www.fwmetals.com/products/strands/assemblies.php, Feb. 7, 2007, (2 pages).

Designing Hypotube Shafts, Design characteristic of Hypotube-Based Shafts, retrieved from www.creganna.com/files/115997863designing_hypotube_shafts.pdf, Oct. 17, 2006, (2 pages).

Notification of Transmittal of the International Search Report and the Written Opinion of the International Searching Authority, or the Declaration mailed Mar. 4, 2009 for corresponding International Application No. PCT/US2008/087130.

Farrissey, L., Metal Shafts: Design to Meet the Required Performance, Medical Device Technology, Dec. 2004.

* cited by examiner

STRUCTURE FOR USE AS PART OF A MEDICAL DEVICE

CROSS-REFERENCE TO RELATED CASES

This application claims priority to, and the benefit of Provisional U.S. Patent Application Ser. No. 61/015,105, filed Dec. 19, 2007, the entirety of which is incorporated herein by reference.

TECHNICAL FIELD

The present invention generally relates to a low cost, flexible, and torqueable structure for use as part of a medical device.

BACKGROUND INFORMATION

Medical devices are commonly used to access remote regions of the body to deliver diagnostic or therapeutic agents to those regions and to perform surgical procedures on those regions. For example, endoscopes may use body airways and canals to access the colon, esophagus, stomach, urethra, bladder, urethra, kidneys, lungs, bronchi, uterus, and other organs. Catheters may use the circulatory system as pathways to access treatment sites near the heart or may use the urinary tract to access urinary regions.

Some medical devices can be introduced into the vasculature of the body of the patient through a large artery such as those found in the groin or in the neck of a human or other mammal. These devices are often passed through ever-narrower arteries until they can reach the operative site inside the body. Many such pathways may curve, loop around, and even wind back.

Catheters are described in various patents, published patent applications, and other publications. See, for example, U.S. Pat. No. 3,924,632 and published U.S. Patent Application 2006/0111649.

SUMMARY OF THE INVENTION

The present invention generally relates to a low cost, flexible, and torqueable structure for use as part of a medical device and also methods of making such a structure. The structure can be manufactured without the use of expensive tubing or costly, time-consuming, and complicated laser cutting operations, and also without the need for one of more layers (of, for example, braided wire or other such material), yet still achieved the desired flexibility and torqueability. The structure can be formed simply of a coiled wire that is fed through a laser cut machine to join or weld together at least some of the adjacent turns of the coil. The laser cut machine would be set to apply an appropriate amount of laser energy to fuse or weld those adjacent turns but not to cut thought the coiled wire, and the coil would be rotated as it is fed longitudinally through the machine to create a winding pattern of weld locations.

In one aspect, the invention features a structure for use as at least a portion of a medical device, and the structure comprises a coil formed of a wound element. The coil includes a plurality of adjacent windings and each winding has a pitch. A material is disposed in a portion of the region between adjacent windings such that the material connects adjacent windings of the coil and allows torque to be transmitted between adjacent windings.

The wound element can be a flat wire, and the flat wire can be metal or other synthetic or natural material. The element typically will be made of one or more materials that are acceptable for use within the body of a patient.

The structure can include an outer sheath disposed over the coil. The outer sheath can be made from a variety of known materials and can be heat shrunk to fit over the coil. The structure can also include and inner tube, disposed in the inside of the coil and with a proximal end and a distal end and a lumen extending from the proximal to the distal end of the coil.

BRIEF DESCRIPTION OF THE DRAWINGS

For a fuller understanding of the nature and operation of various embodiments according to the present invention, reference is made to the following description taken in conjunction with the accompanying drawing figures which are not necessarily to scale and wherein like reference characters denote corresponding or related parts throughout the several views.

DESCRIPTION

As indicated above, the present invention relates to a flexible and torqueable structure for use as part of a medical device. Such a structure can be manufactured without the use of expensive tubing or costly, time-consuming, and complicated laser cutting operations, and also without the need for one of more layers, yet still achieved the desired flexibility and torqueability.

Figures 1, 2:
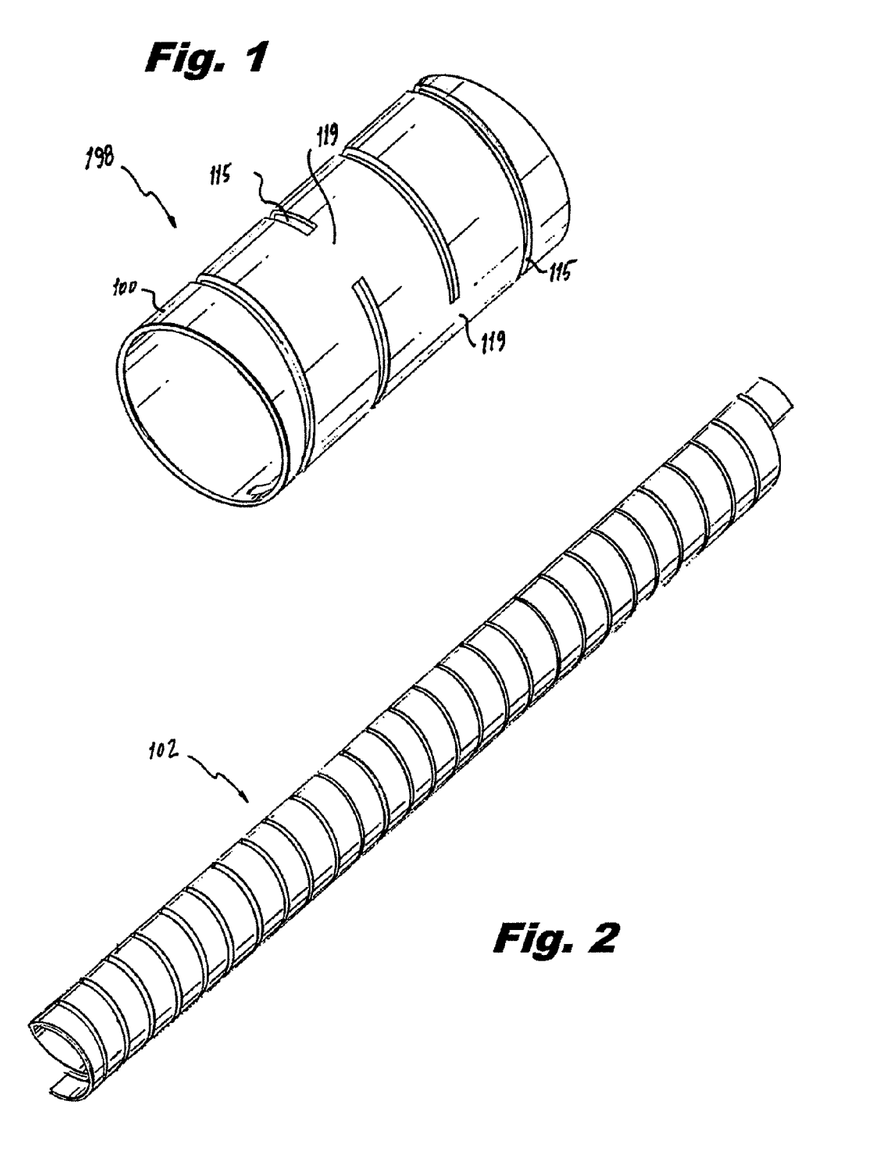
FIG. 1 is a diagram of a section of laser cut tubing.
FIG. 2 is a diagram of a coil.

Referring now to FIG. 1, a structure 198 for use as at least part of a medical device comprises a tube 100 that is laser cut for the purpose of producing a flexible torqueable hollow shaft. The laser cutting is made in a spiral path with alternating cut 115 and un-cut 119 portions. The cut pattern is specified by the pitch and the length of the cut 115 and un-cut 119 portions.

The length of the cut 115 portion of the spiral path is generally several times greater than the un-cut 119 portion. The spiral path of the cut 115 and un-cut 119 portions can be specified in terms of the radial angle. The cut pattern can be defined by the pitch and the radial angle of the cut and un-cut portions. For example, the pattern shown in FIG. 1 has a pitch of 0.035" and the cut/un-cut portions are specified as 220°/45°. The length and width of the cuts, as well as the relative ratio of cut-to-uncut portions can be varied to impart different flexibilities at different parts of the structure 198. Stainless steel tubing with such laser is available from Creganna Medical Device Company of Parkmore West, Galway, Ireland.

Referring now to FIG. 2, a flat-wire wound coil 102 is shown. The coil 102 can be formed by winding a flat wire into a tubular shape. The coil 102 is flexible, but does not transmit torque well from one end of the coil to the other end.

Figure 3:
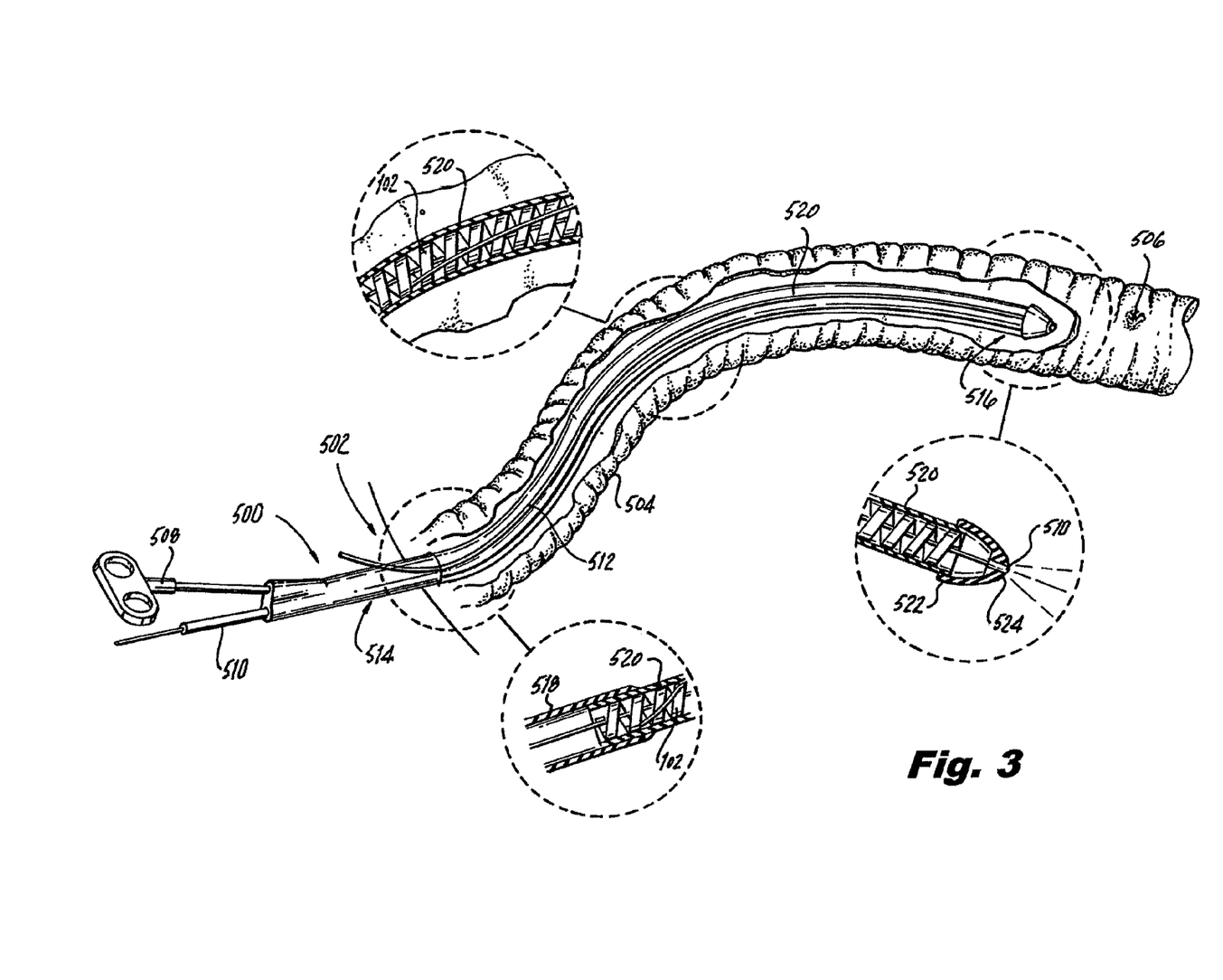
FIG. 3 is a diagram depicting the a coil used as part of an endoscope.

The coil 102 can be used as a portion of a medical device 500 such as an endoscope as shown in FIG. 3. The coil 102 can impart flexibility to the endoscope 500, as it makes its way from the exterior body opening 502, through the body pathway 504, and to the operative site 506.

The endoscope 500 can include a surgical component 508 and an imaging component 510. Any of a variety of surgical components can be passed into a working channel of the endoscope 500 including biopsy forceps, snares, fulguration probes, and other tools. The imaging component 510 can produce an image that is displayed to an operator of the endoscope 500. The imaging component 510 can include an objective lens and fiber optic imaging light guide communicating with a camera located at a proximal end 514 of the endoscope 500, or an imaging camera chip at a distal end 516. The endoscope 500 can be run over a guide wire 512 to facilitate placement of the endoscope within a patient. The terms proximal and distal require a point of reference. In this application, the point of reference is the perspective of the user. Therefore, the term proximal will always refer to an area closest to the user, whereas distal will always refer to an area away from the user.

The endoscope 500 may be uniformly flexible or could comprise a plurality of segments having varying degrees of flexibility or rigidity. The endoscope 500 includes an outer sheath 520 disposed on the outside of the flexible coil 102 to provide a smooth exterior surface. The outer sheath 520 can be made from soft, thin polyurethane, LLDPE, silicon, pellethane, polyurethane or other approved biocompatible materials such as polyethylene, polypropylene or polyvinyl alcohol. Additionally, the outer sheath 520 can be coated with a hydrophilic, lubricious coating such as HYDROPASS™ hydrophilic coating available from Boston Scientific Corporation, of Natick, Mass., and described in U.S. Pat. Nos. 5,702,754 and 6,048,620, which are herein incorporated by reference.

The coil 102 could also be used as at least a portion of a catheter, and the catheter can include an infusion pump for pumping liquids to a site within the body. The coil 102 also could be used as at least a portion of a medical stent.

Some endoscopes and catheters have means for steering or deflecting the distal tip of the endoscope to follow the pathway of the anatomy under examination such as the colon, bladder, kidney, and heart. Deflection or articulation is often a desirable characteristic in these types of medical devices to minimize friction force and trauma to the surrounding tissue, and to survey targeted examination sites. Navigation of the endoscope through various areas within a patient improves the success of the examination and minimizes pain, side effects, risk, or sedation to the patient. Therefore, in addition to imparting flexibility to endoscope or a catheter, it would be desirable to provide a coil that is flexible, but also one that has the ability to transmit torque from the proximal end of the coil to the distal end.

Figures 4, 5:
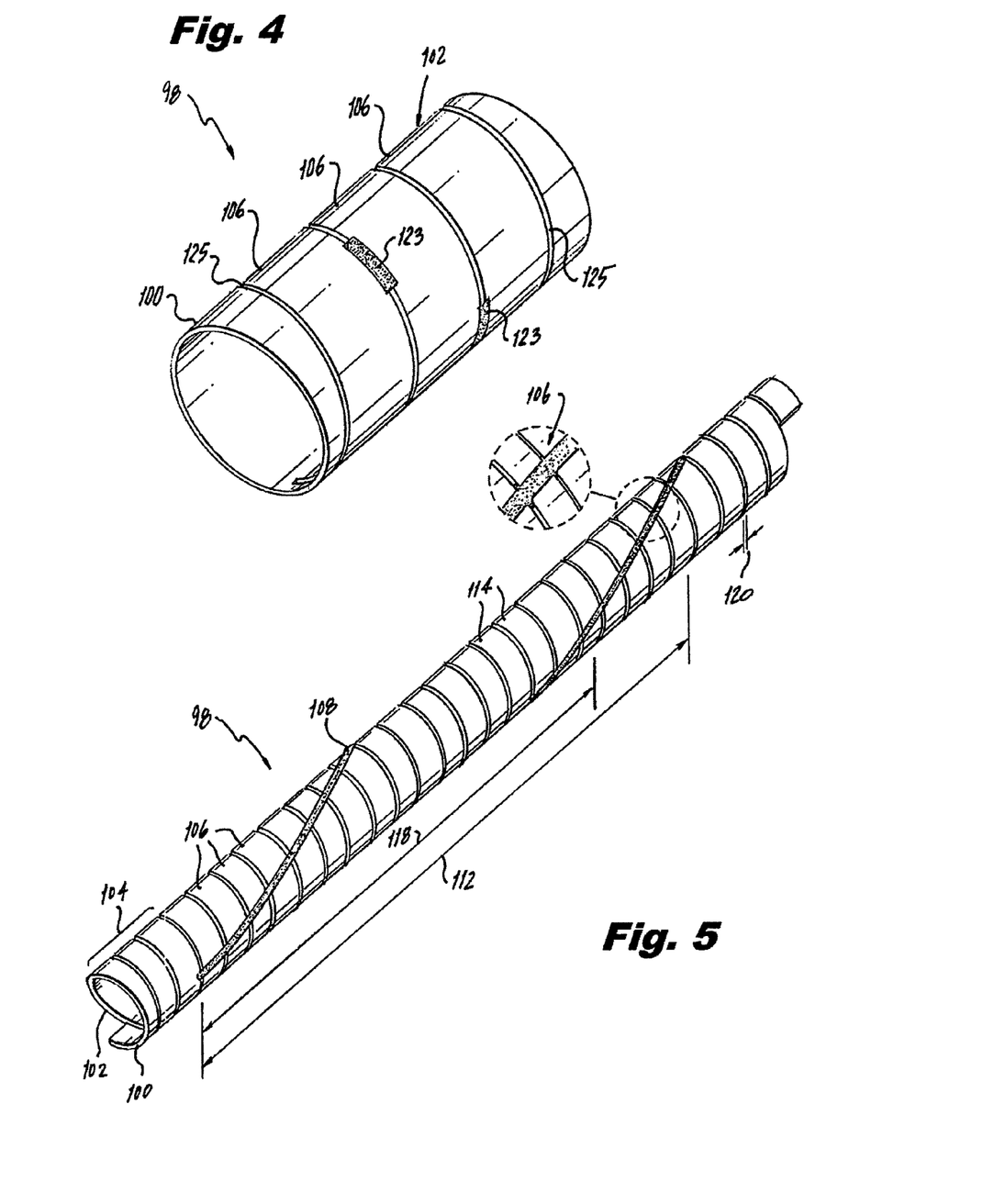
FIG. 4 is a diagram depicting one aspect of the low cost, flexible, torqueable structure.
FIG. 5 is a diagram depicting an alternative embodiment of the low cost, flexible, torqueable structure.
Figures 6A, 6B, 6C, 6D, 6E:
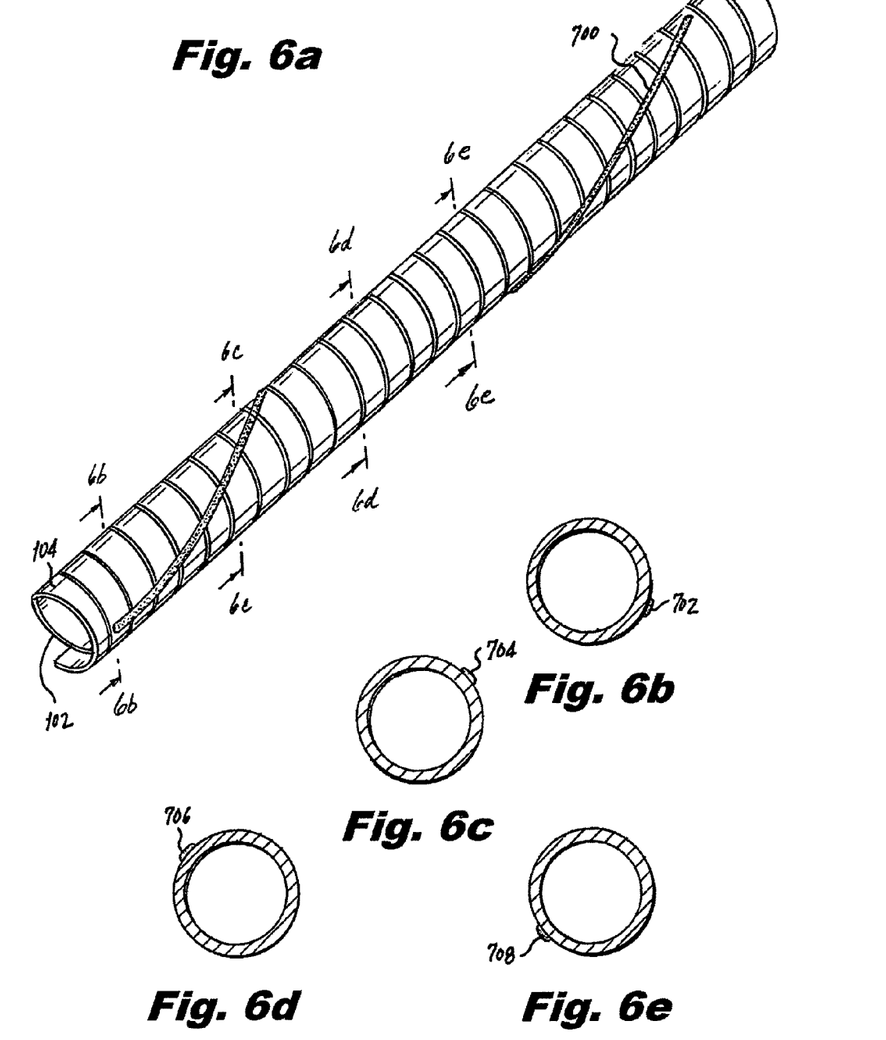
FIGS. 6a-6e are diagrams of the structure of FIG. 5 depicting the material disposed windingly along the outer surface of the coil.

FIG. 4 shows an alternative embodiment of a structure 98 for use with a medical device. The structure 98 performs a similar function as the structure 198 described above. In this embodiment, the structure 98 comprises an element 100 that is wound into a coil 102. The element 100 can be, for example, a flat wire with a rectangular cross-section. The flat-wire can have a rectilinear profile or can have rounded edges. In one embodiment, the width of the flat-wire can be varied to control the flexibility and torqueability along a length of the coil. In another embodiment, the width can be held constant to produce uniform flexibility and torqueability along a length of the coil. The thickness of the flat-wire can also be varied to control the flexibility and torqueability along a length of the coil or can be held constant to produce uniform flexibility and torqueability along a length of the coil. In short, the element 100 that is wound to form the coil 102 can have a variety of widths and cross-sectional shapes and the shape can vary along the length of the coil 102.

The element 100 can be made of any of a variety of materials, including metallic materials that offer superior strength-to-weight rations. Examples of metals include stainless steel and tungsten alloys, and other more malleable alloys, including gold, platinum, palladium, rhodium, etc. The class of alloys know as super-elastic alloys can also be used, including titanium. Other materials, including synthetic and natural materials, can also be used, such as plastic. The element 100 typically will be made of one or more materials that are acceptable for use within the body of a patient.

The coil 102 can be manufactured using any of a number of methods, including winding the element around a barrel forming a plurality of windings 106. A portion of the region between adjacent windings are then welded or otherwise adhered to each other to form connected 123 and unconnected 125 portions. The connected portions 123 and unconnected portions 125 shown in FIG. 4 are similar to the uncut 119 portions and cut 115 portions shown in FIG. 1, respectively, in that the unconnected portions 125 behave essentially the same as the cut portions 115 and the connected portions 123 behave essentially the same as the uncut portions 119.

The process of connecting some of the region between adjacent windings can be accomplished with a laser in a similar manner as the laser cutting of tubing described above. The wound coil 102 can be continuously fed into a laser welding machine and be welded in a spiral path with alternating welded and unwelded portions. The performance of the welded coil structure 98 would be similar to cut tube structure 198 described above.

One advantage of the welded structure 98 over the cut tubing structure 198 is the manufacturing time on the laser cutting/welding machine. In order to provide the greatest amount of flexibility, the radial angle of the cut/unwelded portion is generally greater than the radial angle of the uncut/welded portion. For example, in FIGS. 1 and 4, the radial angle of the cut/unwelded portion is 220° and the radial angle of the uncut/welded portion is 45°, i.e., almost 5 times greater. Therefore, the time spent laser cutting a tube would be almost 5 times longer than the time laser welding the wound tube. This reduced manufacturing time translates into reduced manufacturing costs.

The material used to make the tubing is also generally different from the flat wire used to make the wound coil. The cost of the material for the cut tubing is generally much higher than that of the wound coil. Also, there is a greater variety of materials for the wound coil so the performance of the structure including flexibility, torqueability, strength and durability, would be superior to the cut tubing design. Finally, the availability of a greater variety of materials might allow for, for example, thinner walls of the structure 98, which translates into a bigger inside diameter and smaller outside diameter which is always a desirable characteristic in medical devices such as endoscopes and catheters.

In another embodiment, the wound coil 102 includes a material disposed on the outer surface of the wound coil 102. Referring now to FIG. 5, the coil 102 includes an outer surface 104, defined by the outer surface of each of the windings 106 of the element 100. A material 108 is disposed windingly on the outer surface 104 of the coil 102, and the material 108 extends longitudinally along a length 112 of the coil 102. The length 112 shown is less than the entire length of the coil 102, but the length 112 could be the entire length of the coil 102 or any portion thereof. The material 108 connects adjacent windings 114 of the coil 102 to each other at a location 116 on the outer surface 104 of the coil 102.

Figure 7:
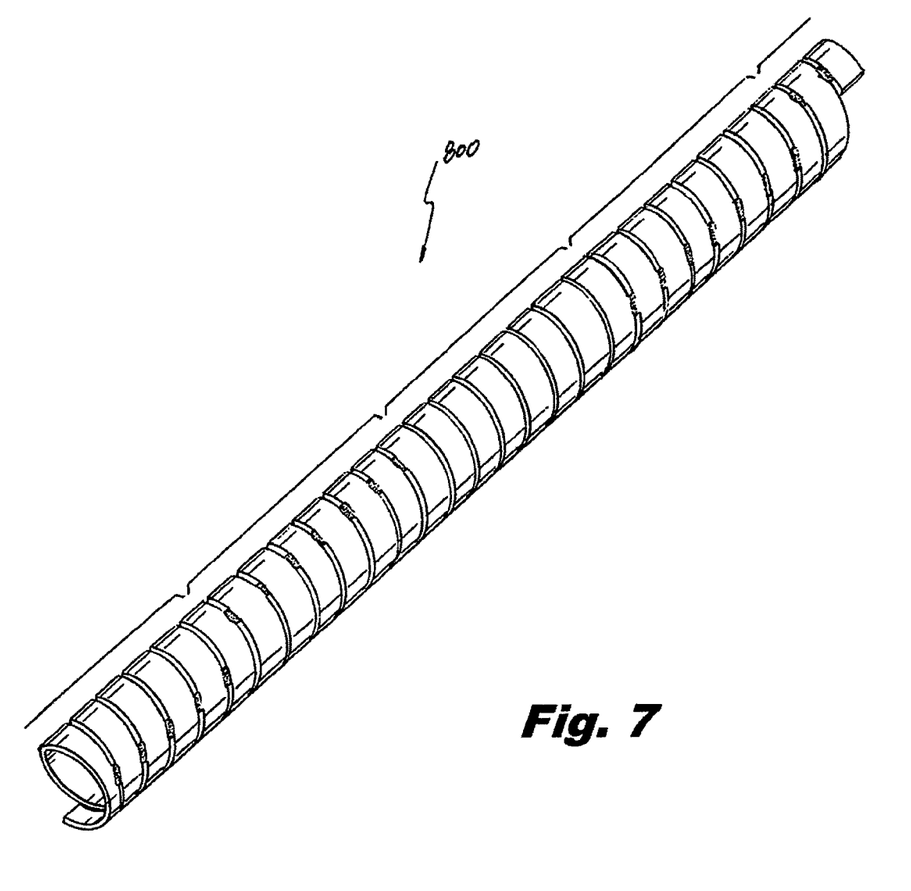
FIG. 7 is a diagram depicting the material disposed in straight lines along the length of the coil.

The material 108 can be disposed using a variety of methods. For example, a weld-applying machine can be used to dispose the material 108 on the outer surface 104 of the coil 102 as the coil is rotated and advanced longitudinally. Referring now also to FIGS. 6a-6e, the material 108 is a strip of material 700 disposed windingly 702, 704, 706, 708 along the outer surface 104 of the coil 102. The material 108 can also be disposed in a straight line or in a series of separate straight lines 800 as shown in FIG. 7. The material 108 can be made from a variety of materials, including, for example, adhesive, solder, or an epoxy.

Figure 8:
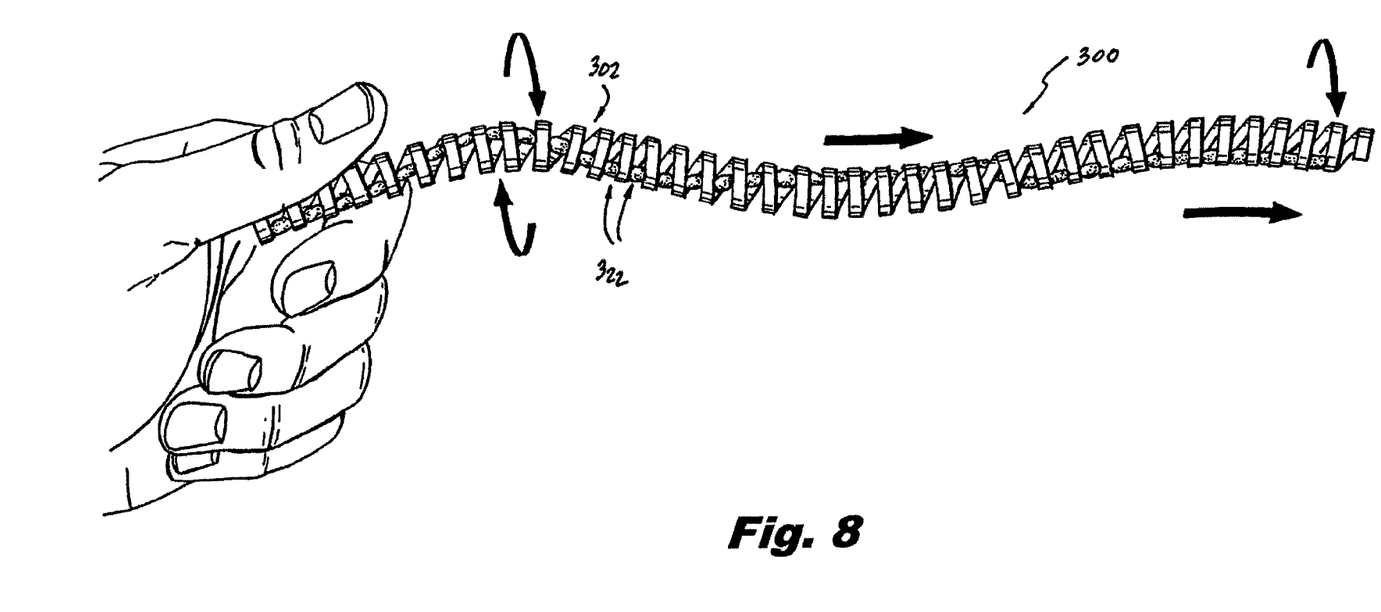
FIG. 8 is a diagram depicting flexing, torqueing, and pushing of the structure.

Referring now to FIG. 8, the material 108 can alternatively be disposed at discrete points along the length of the coil 102. A laser spot welding machine can dispose the material 108 on the outer surface of the coil to connect adjacent windings of the coil. The material disposed along the windings of the coil produces a structure that is flexible 300 and torqueable 302.

Figure 9:
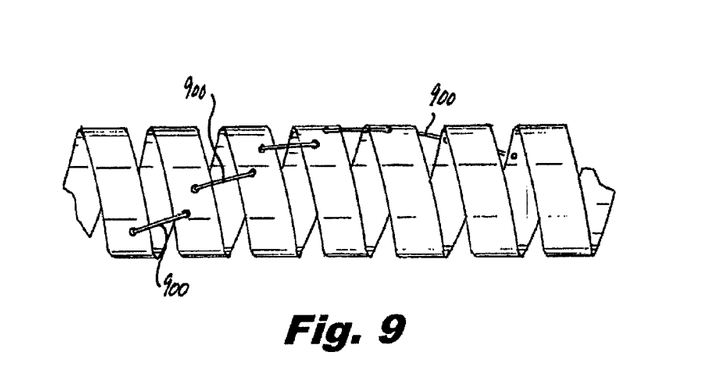
FIG. 9 is a diagram depicting a plurality of rivets connecting adjacent windings of the coil.

In other embodiments, the material 108 can be a connecting element, including a rivet or a hinge. As shown in FIG. 9, the material 108 can be a plurality of rivets 900 connecting the adjacent windings of the coil.

Figure 10A:
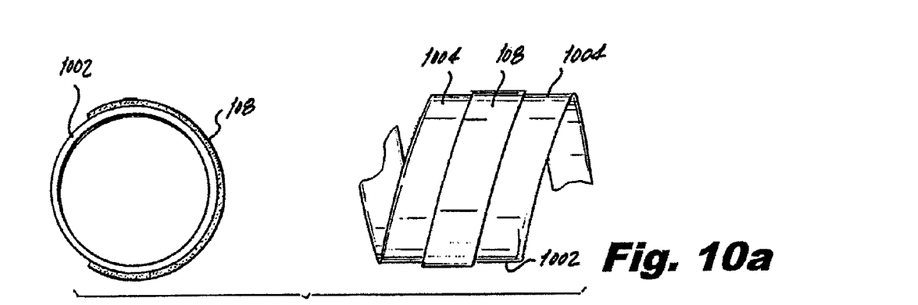
FIG. 10a is a diagram depicting the material connecting a portion of the space on the outer surface of the windings of the coil, the connected portion being greater than the unconnected portion.
Figure 10B:
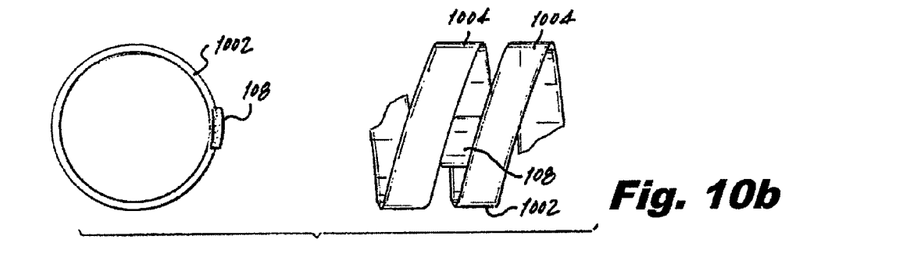
FIG. 10b is a diagram depicting the material connecting a portion of the space on the outer surface of the windings of the coil, the connected portion being smaller than the unconnected portion.

In some embodiments, the material 108 can connect a portion of the outer surface 1002 of the adjacent windings 1004 of the coil that is longer than an unconnected portion of the outer surface 1002 of the adjacent windings 1004 of the coil as shown in FIG. 10a. Alternatively, as shown in FIG. 10b, the material 108 can connect a portion of the outer surface 1002 of the adjacent windings 1004 of the coil that is shorter, or equivalent to the unconnected portion of the outer surface 1002 of the adjacent windings 1004 of the coil.

Figure 11:
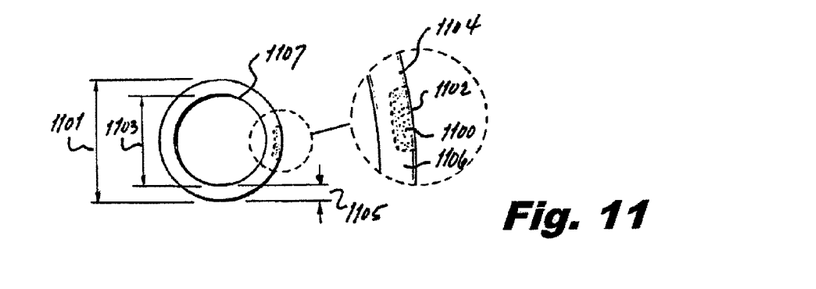
FIG. 11 is a diagram depicting the material flush with the outer diameter of the coil.

The outer diameter of the coil 1101 can be defined as the cross-sectional width of the coil from one side of the outer surface of the coil to the opposite side of the outer surface of the coil. The material 1100 can be disposed in between the windings of the coil along a length of the coil. In one embodiment, the material disposed in between the windings can be designed to be flush 1102 with the outer surface 1104 of the coil 1106, as shown in FIG. 11. This minimizes the outer diameter of the coil 1101, which can reduce the overall diameter of the medical device, thus making the medical device capable of use in smaller body pathways. The outer diameter of the coil 1101 can also be varied along the length of the coil.

Figures 12, 13A:
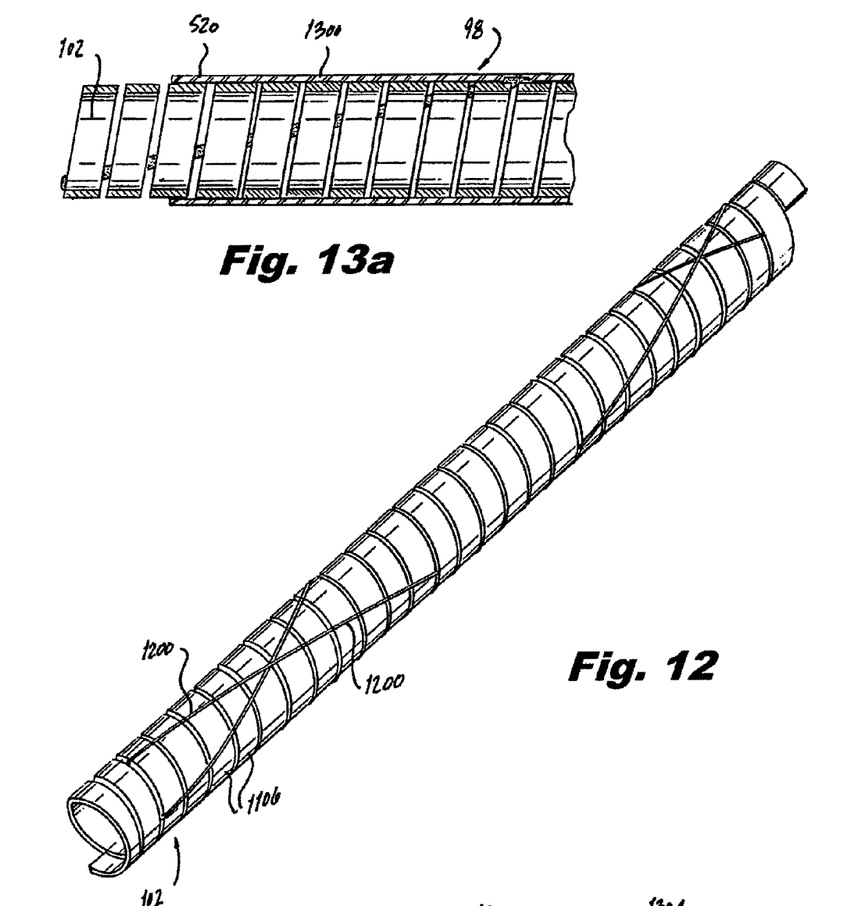
FIG. 12 is a diagram depicting a plurality of strips of the material disposed windingly along the coil.
FIG. 13a is a diagram depicting the structure with an outer sheath.

In one embodiment shown in FIG. 12, a plurality of strips of material 1200 can be disposed on the outer surface 104 of the coil 102, each strip disposed in a different configuration from the other strips, and extending longitudinally along a length 112 of the coil 102. The strips of material connect along a length 112, adjacent windings 106 of the coil 102. Each strip of the material can be divided into a plurality of separate segments connecting adjacent windings 106 of the coil 102.

As shown in FIG. 13a, the structure 98 can include an outer tubing or sheath 520. The outer tubing 520 can provide an outer surface 1300 of the structure 98 that can be, for example, hydrophobic and lubricious. The outer surface 1300 can be a lubricious material, such as Teflon, for example. The outer tubing 520 can be produced of a polymer, which can include polyethylene, polyvinyl chloride (PVC), Pebax, silicone, co-polymers, and other polymers. The outer tubing 520 can be heat shrunk over the coil 102 into tight engagement with the coil 102 and the overall structure 98. Alternatively, the outer tubing can be secured to the coil with an adhesive applied on the outer surface of the coil or at various affixation points on the outer surface of the coil. The adhesive can be a thermoplastic adhesive that softens at the temperature necessary to heat shrink the outer tubing.

Figure 13B:
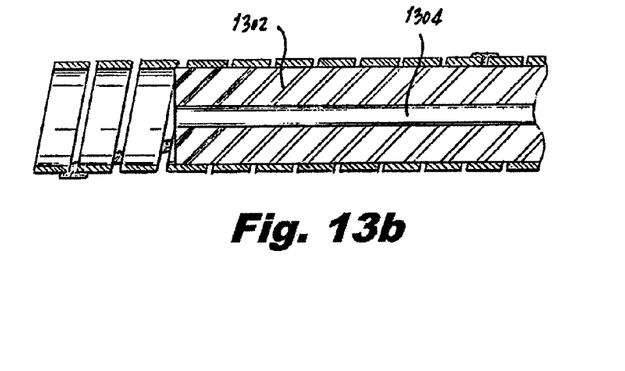
FIG. 13b is a diagram depicting the structure with an inner core.

The structure 98 can include an inner core 1302 which can be solid or hollow, as shown in FIG. 13b. The inner core 1302 can include a working channel lumen 1304. The inner core 1302 can contain additional reinforcing material to further control flexibility and torqueability of the structure. The inner core 1302 can be produced of a polymer, which can include polyethylene, polyvinyl chloride (PVC), Pebax, silicone, co-polymers, and other polymers.

Coil structures according to the invention have a variety of advantages over known structures. Although a welded or joined coil structure in accordance with the invention may be less flexible than a plain coil that is unwelded or unjoined, such as the plain coil shown in FIG. 2, a coil structure according to the invention (such as the embodiments shown in and described herein with reference to FIGS. 3, 5, 6a-6e, 7, 8, 9, 10a and 10b, 11, 12, and 13a and 13b) can transmit torque effectively. This ability to effectively transmit torque tends to enhance the pushability and steerability of a medical device which incorporates a coil structure according to the invention as the device or at least a distal end or distal portion of the device where the inventive coil structure is located is advanced through body pathways 504 of a human or other mammal. For example, as shown in FIG. 8, the coil structure can transmit torque 302 along the welds 322 connecting adjacent windings of the coil and yet also can be flexed 300 along unwelded portions of the windings of the coil. In contrast, a plain coil typically does not transmit torque well as it is rotated.

While certain embodiments according to the invention are shown and described, other embodiments are within the scope of this disclosure and are considered to be part hereof. The invention is not to be limited just to certain embodiments shown and/or described.

What is claimed is:

1. A structure for use as at least a portion of a medical device comprising:
    a coil formed of a wound element, the coil including a plurality of adjacent windings; and
    a material disposed in at least a portion of a region axially between adjacent windings, the material connecting adjacent windings of the coil and thereby allowing torque to be transmitted between adjacent windings.

2. The structure of claim 1 wherein the element comprises a flat wire, the flat wire having a width and a thickness.

3. The structure of claim 2 wherein the flat wire comprises metal.

4. The structure of claim 1 wherein the material comprises a laser weld.

5. The structure of claim 1 wherein the material is a plurality of separate segments of material.

6. The structure of claim 1 wherein the material is a continuous strip of material.

7. The structure of claim 1 wherein the material comprises an adhesive.

8. The structure of claim 1 wherein the material comprises solder.

9. The structure of claim 1 wherein the material comprises epoxy.

10. The structure of claim 1 wherein the material is a plurality of rivets.

11. The structure of claim 1 further comprising an outer sheath disposed over the coil.

12. The structure of claim 11 wherein the sheath is heat shrunk to fit over the coil.

13. The structure of claim 1 further comprising an inner tube, wherein the coil fits over the inner tube.

14. The structure of claim 1 wherein the coil has a proximal end and a distal end and a lumen extending from the proximal end to the distal end of the coil.

15. A structure for use as at least a portion of a medical device comprising:
   a coil formed of a wound element, the coil including an outer surface defined by the outer surface of each of the windings of the element and an axial gap extending axially between adjacent windings; and
   a material disposed windingly on the outer surface of the coil and in a portion of the axial gap along a length of the coil, the material connecting, along the length, adjacent windings of the coil to each other.

16. A structure for use as at least a portion of a medical device comprising:
   a coil formed of a wound element; and
   a material disposed in a winding pattern along a length of the coil and in an axial gap between at least some of the adjacent windings of the coil, the material connecting, along the length, at least some of the adjacent windings of the coil to each other.

17. A method of making a structure for use as at least a portion of a medical device comprising:
   disposing a strip of material windingly on an outer surface of a coil formed of a wound element and having a plurality of windings, the outer surface of the coil being defined by an outer surface of each of the windings of the coil, the strip of material being disposed such that the strip of material extends along a length of the coil and connects adjacent windings of the coil to each other along the length.

18. A method of making a structure for use as at least a portion of a medical device comprising:
   disposing a strip of material in a winding pattern along a length of a coil formed of a wound element and between at least some of the adjacent windings of the coil such that the strip of material connects the at least some of the adjacent windings of the coil to each other.

* * * * *